(12) United States Patent
Charles, Jr. et al.

(10) Patent No.: US 8,758,241 B2
(45) Date of Patent: Jun. 24, 2014

(54) ELECTRONIC MODULE WITH KEYED CONNECTION TO A WEARABLE GARMENT FOR MONITORING PHYSIOLOGICAL FUNCTIONS AND METHOD OF USE

(75) Inventors: Harry K. Charles, Jr., Laurel, MD (US); Russell P. Cain, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 1314 days.

(21) Appl. No.: 12/503,600

(22) Filed: Jul. 15, 2009

(65) Prior Publication Data
US 2010/0016681 A1 Jan. 21, 2010

Related U.S. Application Data

(60) Provisional application No. 61/080,704, filed on Jul. 15, 2008.

(51) Int. Cl.
*A61B 5/04* (2006.01)
*H05K 7/00* (2006.01)
*A61B 5/05* (2006.01)
*A61B 5/00* (2006.01)
*G06K 19/00* (2006.01)
*H05K 3/00* (2006.01)

(52) U.S. Cl.
CPC .... *A61B 5/0002* (2013.01); *H05K 2201/10037* (2013.01); *H05K 3/0058* (2013.01); *H05K 2201/10151* (2013.01); *A61B 5/6804* (2013.01)
USPC ............... 600/301; 600/393; 29/592; 29/601; 235/1 R; 235/488; 235/492; 439/37; 439/374; 361/600; 361/679.01; 361/728; 361/737

(58) Field of Classification Search
None
See application file for complete search history.

(56) References Cited

U.S. PATENT DOCUMENTS 5,321,240 A * 6/1994 Takahira ..................... 235/380
5,480,842 A * 1/1996 Clifton et al. ................. 438/464
5,572,401 A 11/1996 Carroll
(Continued)

FOREIGN PATENT DOCUMENTS

JP 0670897 3/1994
WO WO 99/64657 12/1999

OTHER PUBLICATIONS

Axisa, F, et al; "Wrist Ambulatory Monitoring System and Smart Glove for Real Time Emotional, Sensorial and Physiological Analysis"; Proceedings of the 26th Annual International Conference of the IEEE EMBS San Francisco, CA, USA, Sep. 1-5, 2004, p. 2161-2164.*

(Continued)

*Primary Examiner* — Bill Thomson
*Assistant Examiner* — Marie Archer
(74) *Attorney, Agent, or Firm* — Noah J. Hayward

(57) ABSTRACT

A plurality of sensors are embedded in a form fitting garment similar to exercise togs such that the sensors are held in contact with or close proximity to the body. The sensors are connected via a plurality wires to an electronics module which is unintrusive being literally in its ultimate configuration the size of a credit card. A range of thickness, from 6 mm (6 credit cards) down to 1 mm or less, is possible for the module inclusive of a rechargeable lithium polymer battery. The electronics module can be easily removed for garment maintenance (laundering).

13 Claims, 9 Drawing Sheets

(56) References Cited

U.S. PATENT DOCUMENTS

| | | | |
|---|---|---|---|
| 5,669,393 A * | 9/1997 | Faisandier | 600/509 |
| 5,749,365 A * | 5/1998 | Magill | 600/484 |
| 6,047,203 A | 4/2000 | Sackner et al. | |
| 6,424,315 B1 * | 7/2002 | Glenn et al. | 343/895 |
| 6,454,708 B1 * | 9/2002 | Ferguson et al. | 600/300 |
| 6,471,087 B1 | 10/2002 | Schusterman | |
| 6,693,513 B2 * | 2/2004 | Tuttle | 340/10.1 |
| 6,774,865 B1 * | 8/2004 | Serra | 343/895 |
| 7,412,281 B2 | 8/2008 | Shen et al. | |
| 7,958,622 B1 * | 6/2011 | Ayala et al. | 29/600 |
| 8,099,794 B2 * | 1/2012 | Carstens | 2/16 |
| 2003/0127126 A1 * | 7/2003 | Yang | 136/251 |
| 2003/0224223 A1 * | 12/2003 | Edwards | 429/7 |
| 2005/0054941 A1 | 3/2005 | Ting et al. | |
| 2005/0285744 A1 * | 12/2005 | Tuttle | 340/572.1 |
| 2006/0211937 A1 | 9/2006 | Eldridge | |
| 2007/0038057 A1 | 2/2007 | Nam et al. | |
| 2007/0073131 A1 | 3/2007 | Ryu et al. | |
| 2007/0178716 A1 | 8/2007 | Glaser et al. | |
| 2007/0290862 A1 * | 12/2007 | Tuttle | 340/572.7 |
| 2009/0054737 A1 | 2/2009 | Magar et al. | |
| 2009/0261778 A1 * | 10/2009 | Kook | 320/108 |
| 2009/0306485 A1 * | 12/2009 | Bell | 600/301 |

OTHER PUBLICATIONS

Axisa, F, et al; "Flexible Technologies and Smart Clothing for CitizenMedicine, Home Healthcare, and Disease Prevention"; IEEE Transactions on Information Technology in Biomedicine, vol. 9, No. 3, Sep. 2005; p. 325-336.*

Smith, T. "Smart Cards: Integrating for Portable Complexity"; Computer, Hewlett-Packard, Aug. 1998, p. 110-115.*

Warren, S. "Wearable Telemonitoring Systems Designed with Interoperability in Mind"; Proceedings of the 25' Annual International Conference of the IEEE EMBS Cancun, Mexico Sep. 17-21, 2003; p. 3736-3739.*

* cited by examiner

ELECTRONIC MODULE WITH KEYED CONNECTION TO A WEARABLE GARMENT FOR MONITORING PHYSIOLOGICAL FUNCTIONS AND METHOD OF USE

CROSS-REFERENCE TO RELATED APPLICATIONS

This application claims the benefit of prior filed U.S. provisional application No. 61/080,704, filed on Jul. 15, 2008, which is incorporated herein by reference in its entirety.

BACKGROUND OF THE INVENTION

1. Field of the Invention

The present invention relates generally to physiological function monitors and, more particularly, to a small, lightweight module for use in conjunction with sensors embedded in clothing and a garment utilizing the same.

2. Description of the Related Art

The need for real-time continuous monitoring of human physiological functions is becoming increasingly important due to the rapidly increasing over 60 population and the desire of baby boomers to monitor their vital signs and stay fit and the general trend in younger generations for fitness training. Also both amateur and professional athletes are pushing their bodies to the limit so real-time monitoring of their health status is of paramount importance.

Real-time monitoring or recording for later reading of physiological function data especially of exercisers and athletes has to be done in a non-intrusive, non-motion inhibiting manner yet it must provide reliable sensing and signal processing to transmit or store relevant information for the individual, coach and/or the physician. Key to this monitoring is the development of electronics matched to an appropriate sensing system.

Clothing containing sensors to monitor bodily physiological functions is not new, however, the major problem to date with electronically active or smart clothing is that the monitoring control and powering electronics always require a relatively large box (electronics plus battery) attached to the clothing or, in some cases, attached to a wrist band or a belt. Wires typically run from the garment containing the sensors to these boxes. Other embodiments have actually embedded these boxes into the garment thus causing difficulties in laundering. In some cases the sensors have to be attached directly to the body, using adhesives or conducting gels, such as is the case with wearable heart monitors.

In light of the above, there is a need for a wearable garment having electronics and sensors that can be configured to provide reliable data while being unintrusive and non-motion inhibiting to the wearer especially during exercising and can be safe during or easily removed for garment cleaning cycles.

SUMMARY OF THE INVENTION

Therefore, the present invention has been made in view of the above problems, and it is an objective of the present invention to eliminate or circumvent many, if not all, of the issues or limitations described above by providing a garment that can measure physiological functions especially during exercise without inhibiting the exerciser and yet is easy to launder after use.

In Applicants' invention a plurality of sensors are held in direct contact or close proximity to the person's body by being embedded in a form fitting garment similar to exercise togs. The sensors are connected via a plurality of embedded wires to an electronics module which is truly unintrusive being in one embodiment substantially the size of a credit card which is inclusive of the rechargeable lithium polymer battery. The electronics module can be easily removed for garment maintenance (laundering).

Therefore, the invention includes an electronics module connected to a plurality of sensors via a plurality of wires for use in a garment to monitor physiological functions, the electronics module comprising: a thin polymer battery; a first thin, multilayer substrate placed on and electrically connected to the battery; and a plurality of thinned integrated circuits placed on the first substrate.

The invention further includes a garment for monitoring a plurality of physiological functions comprising: a plurality of sensors for measuring the plurality of physiological functions, the sensors being embedded in the garment; an electronics module, the electronics module being substantially the size of a credit card, held in a pocket formed in the garment, and detachably connected to the plurality of sensors by a plurality of wires, the plurality of wires being woven into the garment; wherein the garment is form fitting in order to hold the plurality of sensors in contact with or close proximity to the body of a person exercising; and wherein the garment is washable upon the electronics module being detached from the plurality of wires and removed from the garment.

The invention further includes a method for monitoring physiological functions comprising: embedding a plurality of sensors in a garment; connecting a plurality of wires to the plurality of sensors; and connecting an electronics module to the plurality of wires, the electronics module comprising: placing a first thin, multilayer substrate on and electrically connecting it to a thin polymer battery; and placing a plurality of thinned integrated circuits on the first substrate.

The invention further includes a method for monitoring a plurality of physiological functions comprising: embedding a plurality of sensors for measuring the plurality of physiological functions in a garment, the garment being form fitting in order to hold the plurality of sensors in contact with or in close proximity to the body of the person exercising; connecting a plurality of wires to the plurality of sensors, the plurality of wires being woven into the garment; detachably connecting an electronics module to the plurality of wires, the electronics module being substantially the size of a credit card and held in a pocket formed in the garment; wherein the garment is washable upon the electronics module being detached from the plurality of wires and removed from the garment.

BRIEF DESCRIPTION OF THE DRAWINGS

These and other objects, features and advantages of the invention will be apparent from a consideration of the following Detailed Description considered in conjunction with the drawing Figures, in which.

DETAILED DESCRIPTION

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail.

The thinned die or integrated circuits discussed below are detailed more fully in U.S. patent application Ser. No. 11/756,816, filed Jun. 1, 2007, which is incorporated herein by reference in its entirety.

It should be noted that while the electronics module and garment of Applicants' invention were developed with exercisers and athletes in mind, the term "exercise" is broadly defined to include any bodily activity that enhances or maintains physical fitness and overall health. Furthermore, Applicants' invention is not to be limited to "exercise" as the invention may also be useful for physiological function monitoring in general.

Figure 1:
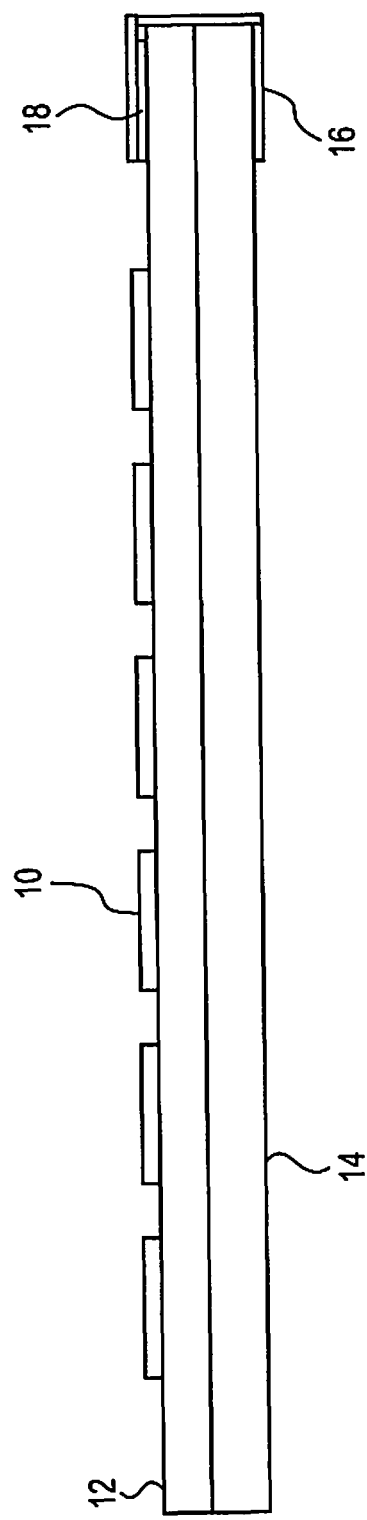
FIG. 1 illustrates a cross-section of the module of the invention.
Figure 2:
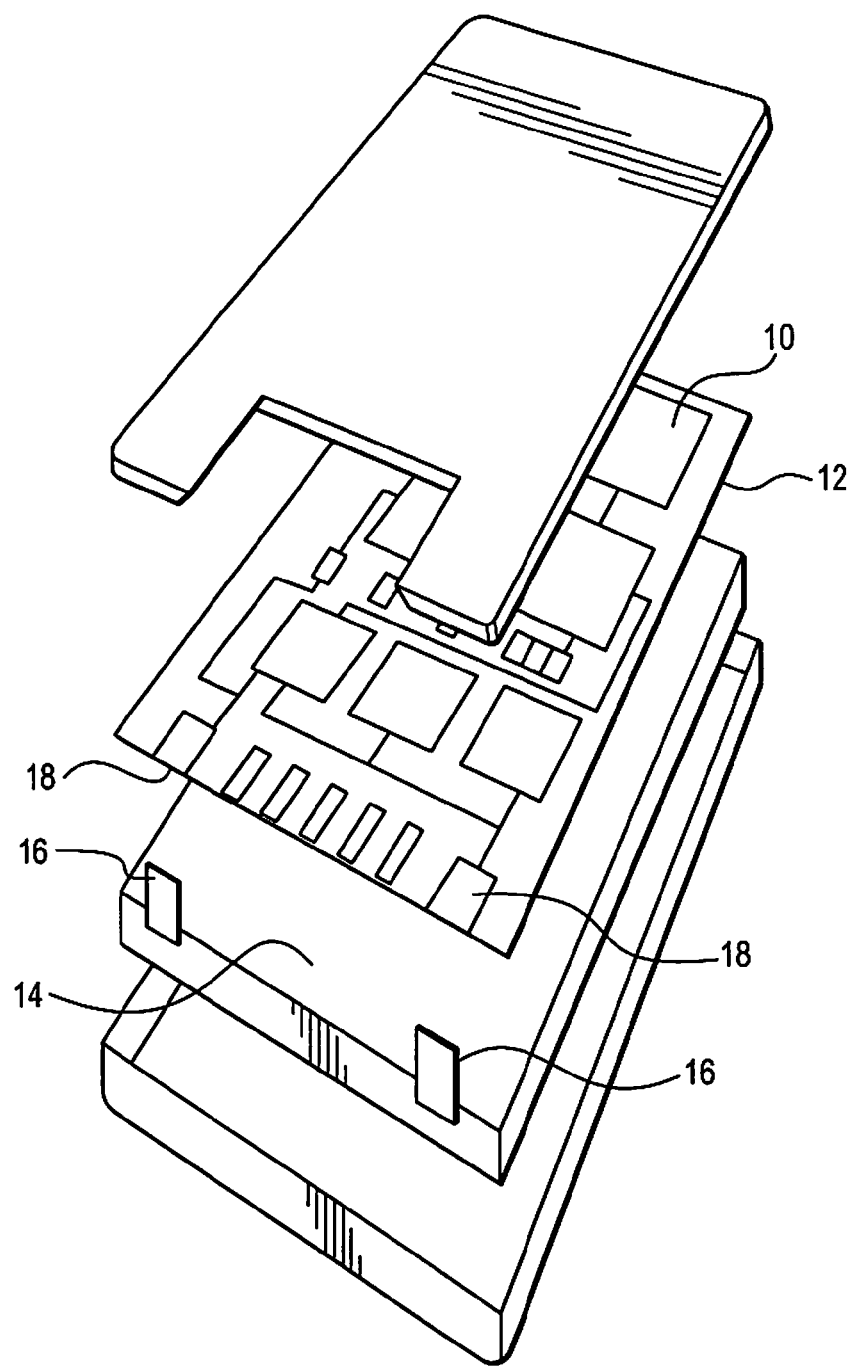
FIG. 2 illustrates an exploded view of the electronics module of the invention.
Figure 3:
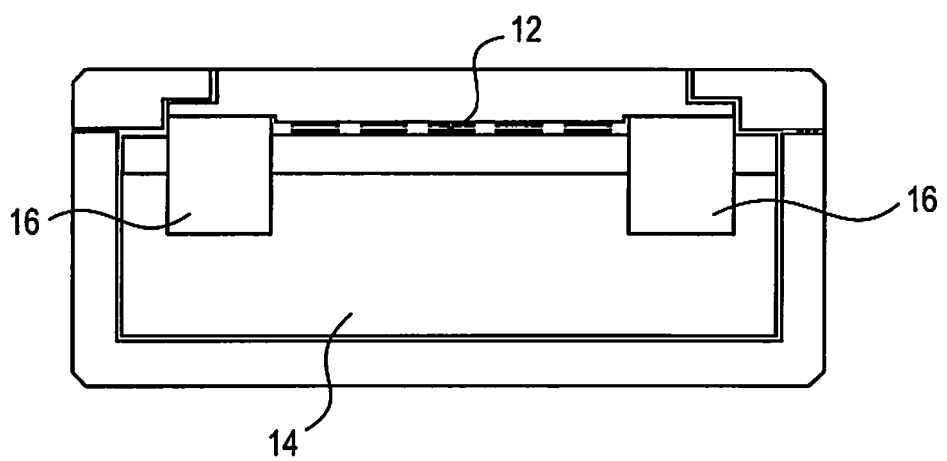
FIG. 3 illustrates an end view of the electronics module of the invention in a case.

FIGS. 1, 2, and 3 illustrate one embodiment of the invention. As noted above, in one embodiment, the electronics module is substantially the size of a credit card, that is, 55 mm W×85 mm L×1 mm H. A range of thickness, from 6 mm (6 credit cards) down to 1 mm or less, is possible for the module depending upon cost targets, the style of electronics (conventional or thinned); frequency and range of transmission; number of functions monitored; module display, if used; and, of course, comfort and ease of use by the wearer. These dimensions are inclusive of a rechargeable lithium polymer battery. While the electronics module is discussed as being in the shape of a credit card, any shape may be possible depending on what is desired and how the electronics module is manufactured.

In addition to its small size, the electronics module is extremely light weight, weighing less than 25 grams (<1 oz) battery included. In the ultimate thin form, the weight will drop below 10 grams.

The module will be highly functional and will have the capability of telemetering a range of physiological function data over a wireless link. The envisioned functionality (sensed physiological functions) and the power budget for each option is given in Table 1.

Table 1 illustrates that with thin rechargeable lithium polymer batteries producing 50 to 200 mAH (which is currently within the capacity of commercially available thin lithium polymer batteries) the unit can be operative for 12 hours to 50 hours before a re-charge would be necessary. This is more than enough time to accommodate a daily exercise routine, a twelve hour bike ride or hiking adventure or even 24 hour to several day heart monitoring activity (using pulse oximetry). In fact, the unit could provide monitoring for several days depending upon the size (thickness) of the polymer battery, the functionality selected and the frequency of transmission events.

For example, using thinned electronics coupled with a thicker polymer battery a 2 credit card thick module (that is, ~2 mm) could last up to two weeks (before a recharge is necessary) depending on how frequently the person monitors and transmits data. The electronics module of the invention is envisioned to have full selectable or deselectable sensors and significant on board storage to simplify data transmission requirements.

Figure 4:
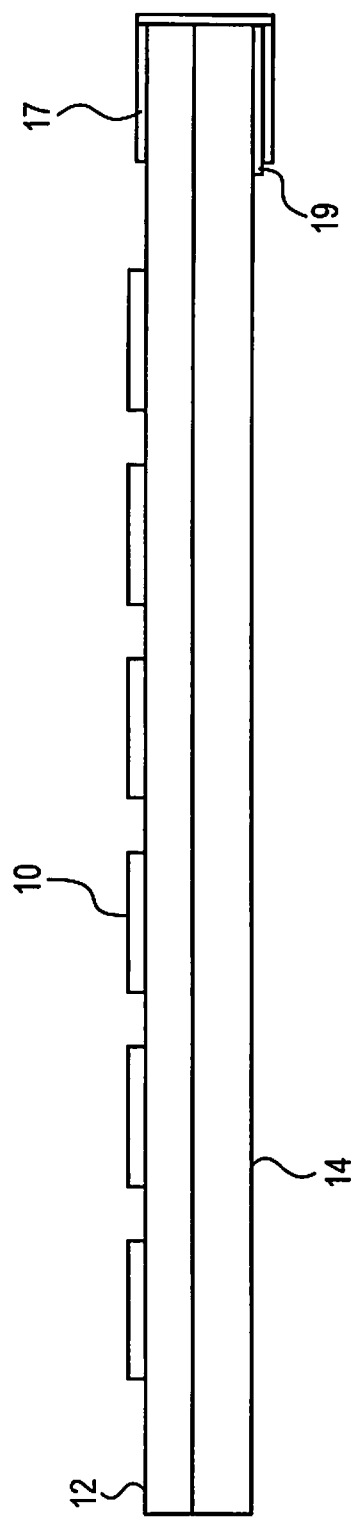
FIG. 4 illustrates a side view of one embodiment of the electronics module of the invention.

As shown in FIG. 1, the electronics module of the invention comprises a thinned die or a plurality of integrated circuits (IC's) 10 with a first double-sided or ultra-thin multilayer (UTML) substrate 12 and a thin polymer battery 14. In one embodiment, shown in FIG. 1, extended flat leads 16 on the battery are wrapped around the UTML substrate to contact surface pads 18 on the UTML substrate. An exploded view of the module in a hardshell case is shown in FIG. 2 and an unexploded cross-section view of the module of FIG. 2 is shown in FIG. 3. In another embodiment shown in FIG. 4, the UTML substrate has leads 17 can be wrapped around the battery to contact the battery contacts/terminals 19. The entire module can be laminated, hardshell encapsulated, or coated with a conformal polymer.

Figure 5:
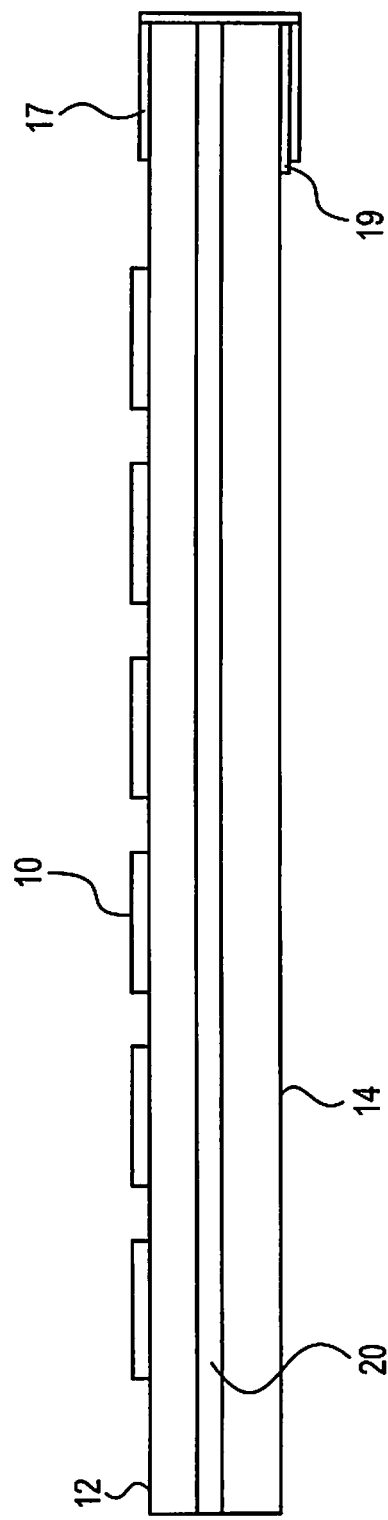
FIG. 5 illustrates a side view of another embodiment of the electronics module of the invention.
Figure 6:
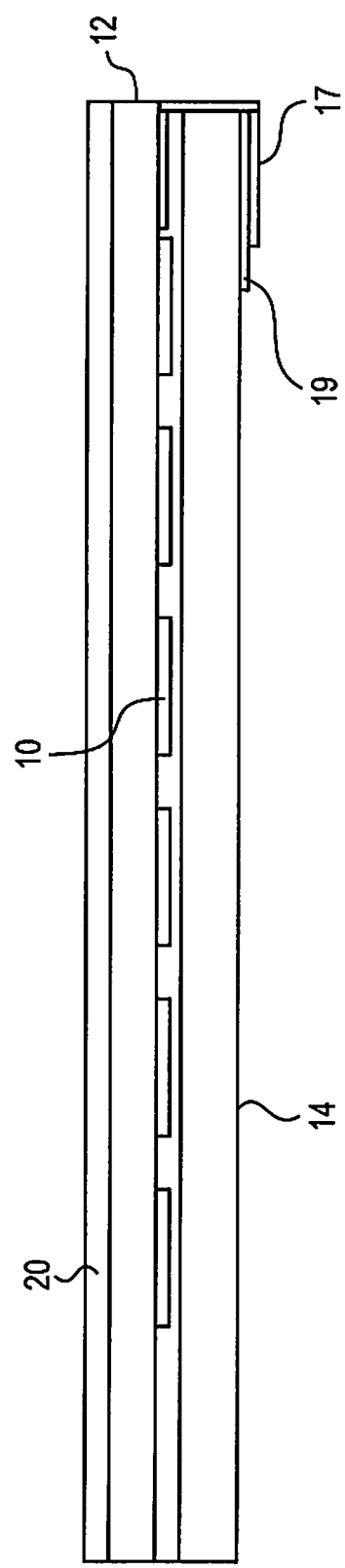
FIG. 6 illustrates a side view of another embodiment of the electronics module of the invention.

As shown in FIG. 5, a metallization layer 20 (typically the bottom layer) of the UTML can be patterned to form an integral antenna (not shown) necessary for wireless communication. This antenna can be placed next to the polymer battery for short range communication or the UTML can be inverted placing the antennas on the top of the module for longer range transmission as shown in FIG. 6. In the standard configuration one of the polymer battery full plane electrode layers could serve as a ground plane for the antenna, if nec-

TABLE 1

Sensor Performance and Analysis

| Sensor | Power (mA @ 3 V) | # of Sensors | Sample Time per Sensor (sec) | Sampling Rate (Hz) | Total Power (mAH @ 3 V) | Modified Weight (gm) |
|---|---|---|---|---|---|---|
| Temperature | 0.14 | 20 | 0.15 | 0.02 | 0.0302 | 10 |
| Humidity | 1 | 20 | 0.15 | 0.02 | 0.2160 | 12 |
| Strain Gauges - Respiration | 0.14 | 2 | 0.15 | 1 | 0.1512 | 1 |
| Acoustics | 0.5 | 8 | 0.15 | 1 | 2.1600 | 10 |
| Pulse - Oximeter | 33.85 | 1 | 10 | 1 | 0.0094 | 21 |
| Galvanometer | 5 | 1 | 1 | 1 | 0.0014 | 5 |
| SHIRT SENSOR SUITE | | | | | 2.5682 | 59 |
| Sphygmomanometer | 3 | 1 | 60 | 0.1 | 0.0001 | 185 |
| Strain Gauges - Movement | 0.14 | 8 | 0.15 | 100 | 60.48 | 10 |
| OPTIONAL SENSORS | | 3 | | | 60.4801 | 195 |
| A/D | 0.5 | 4 | 121 | 1200 | 0.6667 | 1 |
| Microcontroller | 0.000022 | 1 | 60 | 60 | 0.0000 | 1 |
| Accelerometer | 0.18 | 1 | 1 | 60 | 0.0030 | 1 |
| Memory | 15 | 1 | 1 | 60 | 0.2500 | 1 |
| Battery (200mAH) | | | | | | 10 |
| ELECTRONICS | | | | | 0.9197 | 14 |
| Total (W/O Optional Sensors) | | | | | 3.4879 | 73 | essary. In addition to antennas, the UTML could have resistive and capacitive layers built in thus saving the precious surface area for active devices.

Figure 7:
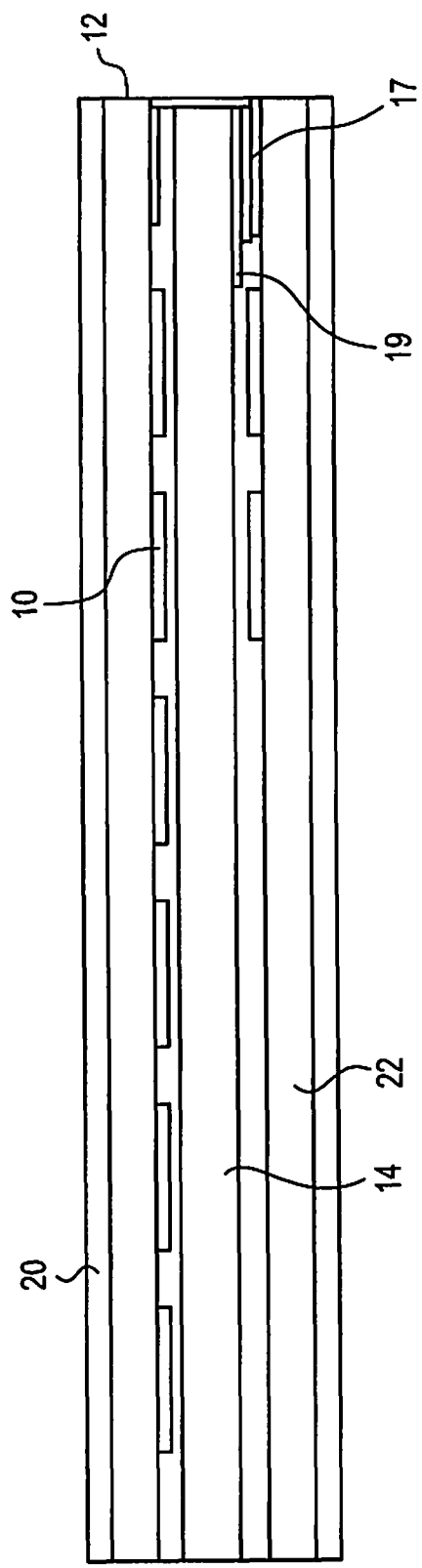
FIG. 7 illustrates a side view of another embodiment of the electronics module of the invention.

In another embodiment shown in FIG. 7, two UTMLs, the first 12 and a second 22 multilayer substrate, can be used in the module, the first containing the thinned die and sensor monitoring circuitry and the second placed on the bottom of the module with the antennas and/or a first inductive loop or coil (not shown) for battery recharging without actual terminal contact. Recharging and perhaps reprogramming of the electronics could be done inductively.

A similar inductive link could be used to power up and communicate with the garment sensors. In this case, a third multilayer substrate (not shown) containing a second inductive coil (not shown) would be sewn into the garment. The matching first inductive coil would be on the surface of the electronics module. When placed in proximity both power and sensor signals can be transferred across the air interface.

Both milli-watts of power and digital signals in the several kilobits per second range can easily be transferred by inductive coils smaller than the credit card outline of the electronics module. With the close proximity, small misalignments will have little effect on power and signal transfer. The first and second inductive coils, the electronics module and garment coils, respectively, can be protected by thin organic layers such as polyimide, acrylic, parylene, and silicon-based resins, thus the second inductive coil will suffer no degradation due to laundering. Similarly, since the electronics module would have no exposed terminals, it would be more suitable for high moisture environments (e.g. perspiration, locker rooms, etc).

Figure 8:
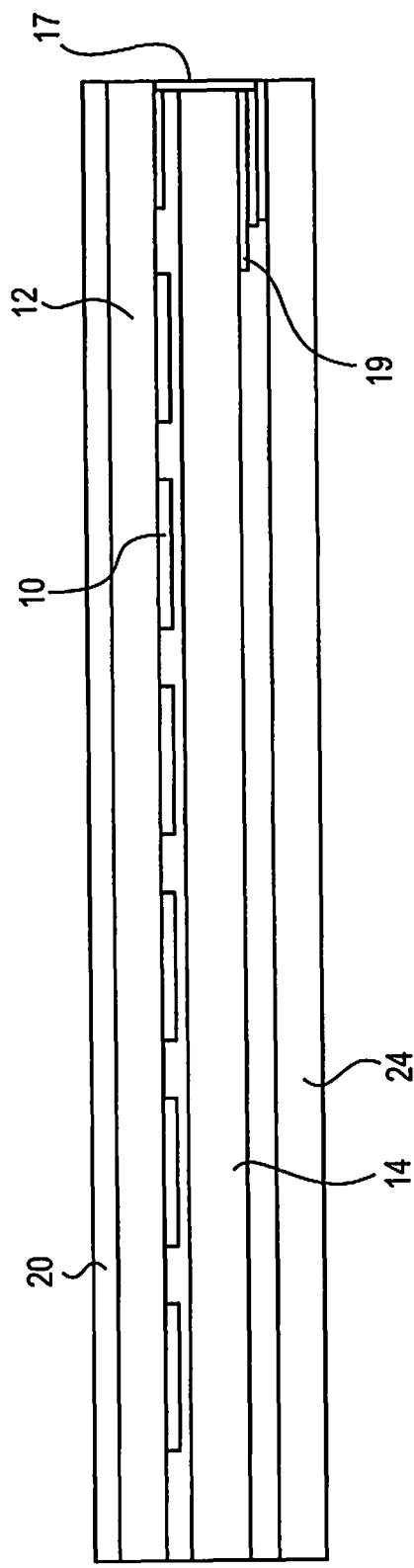
FIG. 8 illustrates a side view of another embodiment of the electronics module of the invention.

Given that silicon can be thinned using techniques referenced above, it is possible to use a thinned solar cell on the back of the module as shown in FIG. 8. An integral solar cell 24 would recharge the battery if exposed to sunlight or even bright ambient light, thus a light transparent pocket in the garment would be necessary. This is easily accomplished for example on the back of cyclist's shirt, or the whole thin flexible system could be laminated to sports helmets. Thinning will reduce the efficiency of the solar cell, but with today's high performance cells, the resulting thinned cells should still have single digit efficiencies more than ample to recharge the electronics module given a credit card sized area.

Figure 9:
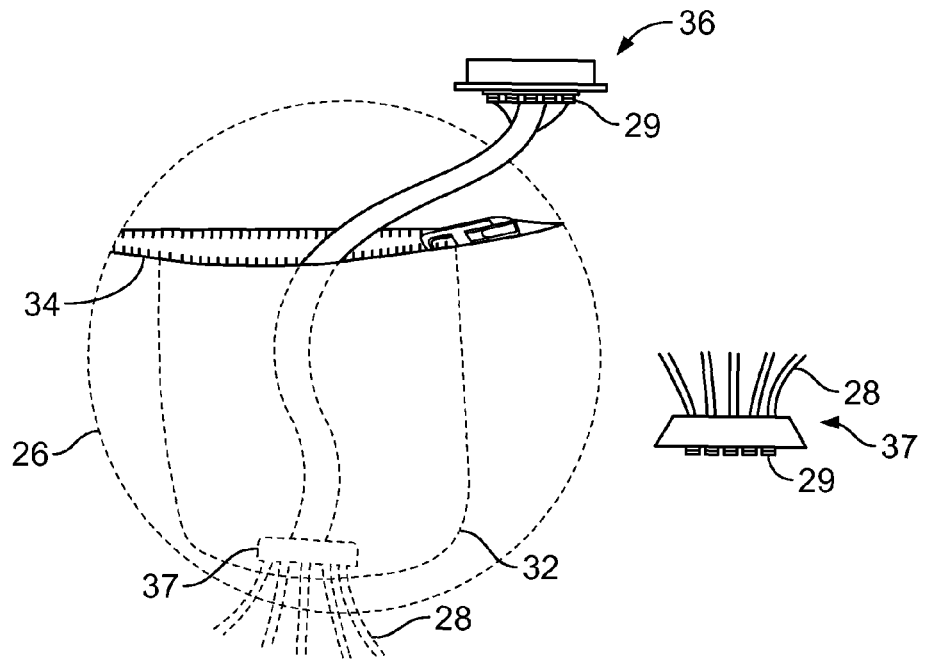
FIG. 9 illustrates both a "T" connector and a wedge connector for connecting the electronics module of the invention to the wires which connect the module to the sensors.
Figure 10:
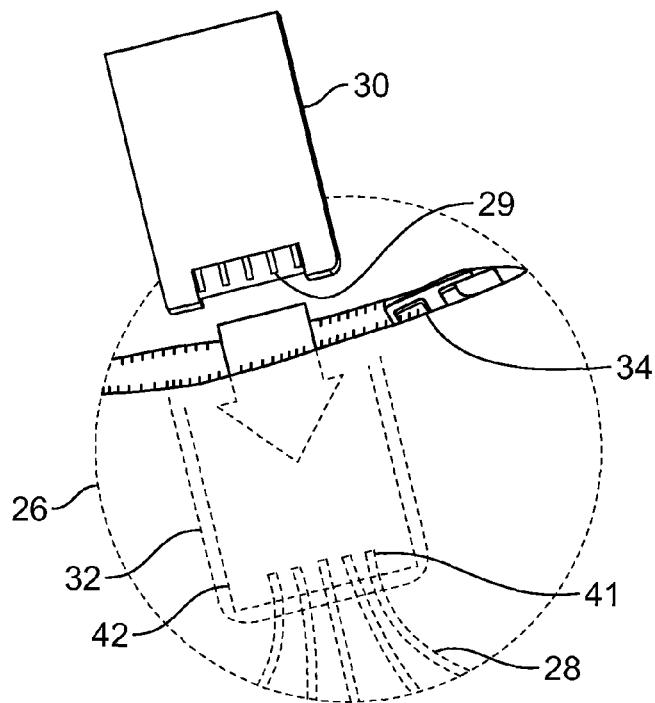
FIG. 10 illustrates a permanent "in pocket" reinforced backing connector for the electronics module of the invention.

A key element in the invention besides its obvious advantages of size, weight, and functionality is its easy attachment and removal from a garment 26 containing a plurality of sensors embedded therein, the sensors being connected to the electronics module via a plurality of wires 28 and electrodes 29. Two examples of the module to garment attachment mechanism are illustrated in FIGS. 9 and 10, but others are possible depending upon garment type, material, and the location of the electronics module attachment point. For most applications it is envisioned that the credit card thin module 30 (FIGS. 1-8) will be placed in a pocket 32 within the garment 26. The pocket 32 will be closed by, for example, a zipper 34 or in another embodiment, VELCRO® (not shown).

One example of the sensor to electronics module attachment is shown in FIG. 9. This method uses a special "T" profile connector 36 which slips into a mating slot on the electronics module edge. The "T" connector 36 is attached to the plurality of sensors by a wedge connector 37 and plurality of wires 28. Sufficient wire slack is allowed so that the "T" connector 36 and module can be connected easily outside of the pocket 32 and then the wire and module are placed in the pocket 32 and the pocket 32 is closed—thus protecting the module during exercise, etc. The "T" connector 36 is keyed for correct insertion in the module and together the module and attached sensor connections would fit snuggly into the garment pocket 32 as mentioned above.

As shown in FIG. 10, an alternate connection scheme comprises a reinforced backing panel 40 placed in the garment pocket 32. This reinforced backing panel 40 would have sensor contacts 41 built in and contain guides 42 to ensure that when the electronics module 30 is inserted into the pocket 32 it makes tight contact with the sensor contacts 41. In this method the user would simply insert the electronics module 30 into the pocket guides 42, push the module 30 into position (seat the module) and then close the pocket 32. Thus, this method eliminates the need for the user to connect wires 28. The module guides 42 are keyed so that the module 30 can only be inserted in the correct direction. In its ultimate configuration, instead of connectors or module guides, optical transmission could be used to interrogate the sensors through embedded fiber optics.

Depending upon the selected mode of readout (wireless or contact) the station for reading and analyzing the data can vary. It can be a base station type where the module is inserted. A connector ("T" type) mounted in the base station engages the sensor contact strip on the module and sends the command to download the stored information. The base station could also have an input device (touchpad/keyboard) to permit reprogramming of the module functions (e.g. change the sampling rate, etc.). In this docking or base station configuration electrodes also engage the battery terminals to recharge the battery at the same time.

If the read out is accomplished remotely via wireless, then the read out and programming would be done on a computer located in the user's home, a doctor's office, or perhaps on the sidelines at a sporting event depending upon the operational scenario. Circuitry has been provided that will uniquely identify and/or serialize each module, thus, enabling a central monitoring station to identify which module is sending the signal.

The electronic modules could be customized for specialized applications such as home or hospital health monitoring, diagnosis, sports and fitness, etc. For example, a simplified version of the electronics module (especially with an integral recharging system (solar cell)) could be mounted on baseball and football helmets to monitor impact strength, head motion, etc. Sensors would include strain gauges and accelerometers. This would be a safety (perhaps a flashing LED) system and would give a quick indication that both the forces received and reactive movements of the head exceeded preset threshold values.

While the invention has been described with reference to example embodiments, it will be understood by those skilled in the art that a variety of modifications, additions and deletions are within the scope of the invention, as defined by the following claims.

What is claimed is:

1. An electronics module connected to a plurality of sensors via a plurality of wires for use in a garment to monitor physiological functions, the electronics module comprising:
a thin polymer battery;
a first thin, multilayer substrate placed on and electrically connected to the battery;
a plurality of thinned integrated circuits placed on the first substrate;
a second thin, multilayer substrate placed on an opposite side of the battery from the first substrate, the second substrate including an antenna patterned thereon and a first inductive coil patterned thereon for inductively recharging the battery and reprogramming the electronics module; and an attachment mechanism for connecting the electronics module to the plurality of wires, wherein
the attachment mechanism is keyed to ensure a proper connection,
the attachment mechanism is permanently installed in a pocket formed in the garment, and
the electronics module is programmed to select or deselect ones of the sensors.

2. The electronics module as recited in claim 1, wherein a portion of the first substrate is extended and wrapped around the battery to contact the battery terminals.

3. The electronics module as recited in claim 1, wherein leads on the battery are extended and wrapped around the first substrate to electrical contacts thereon.

4. The electronics module as recited in claim 1, the first substrate having a plurality of resistive and capacitive layers formed therein thereby providing more surface area for active devices contained in the plurality of thinned integrated circuits.

5. The electronics module as recited in claim 1, further comprising an antenna.

6. The electronics module as recited in claim 5, wherein the antenna is patterned on a layer of the first substrate that is disposed farthest away from the battery.

7. The electronics module as recited in claim 1, further comprising means for wirelessly transmitting physiological data received from the plurality of sensors.

8. The electronics module as recited in claim 1, wherein the thinned integrated circuits further include circuitry configured to enable the electronics module to communicate with a base station configured for receiving the electronics module after the electronics module is detached from the plurality of wires to download the physiological data therefrom.

9. The electronics module as recited in claim 1, further comprising a solar cell, the solar cell being thinned and placed on the battery.

10. A method for monitoring physiological functions comprising:
embedding a plurality of sensors in a garment;
connecting a plurality of wires to the plurality of sensors;
connecting an electronics module to the plurality of wires; and
programming the electronics module to select or deselect ones of the sensors, the electronics module comprising:
a thin polymer battery;
a first thin, multilayer substrate placed on and electrically connected to the battery; a plurality of thinned integrated circuits placed on the first substrate;
a second thin, multilayer substrate placed on an opposite side of the battery from the first substrate, the second substrate including an antenna patterned thereon and a first inductive coil patterned thereon for inductively recharging the battery and reprogramming the electronics module; and
an attachment mechanism for connecting the electronics module to the plurality of wires, wherein
the attachment mechanism is keyed to ensure a proper connection, and
the attachment mechanism is permanently installed in a pocket formed in the garment.

11. The method as recited in claim 10, further comprising patterning an antenna on a layer of the first substrate that is disposed farthest away from the battery.

12. The method as recited in claim 10, wherein the electronics module further comprises means for wirelessly transmitting physiological data received from the plurality of sensors.

13. The method as recited in claim 10, wherein the electronics module further comprises a solar cell, the solar cell being thinned and placed on the battery.

* * * * *